US005994514A

United States Patent [19]
Jardieu et al.

[11] Patent Number: 5,994,514
[45] Date of Patent: Nov. 30, 1999

[54] IMMUNOGLOBULIN VARIANTS

[75] Inventors: Paula M. Jardieu, Berkeley; Leonard G. Presta, San Francisco, both of Calif.

[73] Assignee: Genentech, Inc., South San Francisco, Calif.

[21] Appl. No.: 08/464,025

[22] Filed: Jun. 5, 1995

Related U.S. Application Data

[63] Continuation of application No. 08/328,596, Oct. 25, 1994, abandoned, which is a continuation of application No. 08/178,583, Jan. 7, 1994, abandoned, which is a continuation of application No. 07/744,768, Aug. 14, 1991, abandoned.

[51] Int. Cl.$^6$ ................................................. C07K 16/00
[52] U.S. Cl. ................. 530/388.22; 530/317; 530/391.7; 530/862; 435/183
[58] Field of Search ............................... 530/387.1, 388.7, 530/389.6, 317, 388.22, 391.4, 862; 435/183

[56] References Cited

U.S. PATENT DOCUMENTS

| | | | |
|---|---|---|---|
| 4,629,783 | 12/1986 | Cosand | ..................................... 530/324 |
| 4,714,759 | 12/1987 | Whitaker, Jr. | . |
| 4,861,579 | 8/1989 | Meyer et al. | . |
| 4,940,782 | 7/1990 | Rup et al. | . |
| 5,428,133 | 6/1995 | Chang | ................................... 530/387.3 |

FOREIGN PATENT DOCUMENTS

| | | |
|---|---|---|
| 255249 | 2/1988 | European Pat. Off. . |
| 263655 | 4/1988 | European Pat. Off. . |
| 156285 | 7/1983 | Japan . |
| 8904834 | 6/1989 | United Kingdom . |
| WO89/04834 | 6/1989 | WIPO . |
| WO89/06138 | 7/1989 | WIPO . |

OTHER PUBLICATIONS

Helm et al., "Blocking of passive sensitization of human mast cells and basophil granulocytes with IgE antibodies by a reconbinant human ε–chain fragment of 76 amino acids" *Proc. Natl. Acad. Sci.* 86:9465–9469 (Dec. 1989).
Helm et al., "Identification of the High Affinity Receptor Binding Region in Human Immunoglobulin E" *Journal of Biological Chemistry* 271(13):7494–7500 (Mar. 29, 1996).
Sutton et al., "The Human IgE Network" *Nature* 366:421–428 (Dec. 2, 1993).
Baniyash et al., "Anti–IgE monoclonal antibodies directed at the $FC_\epsilon$ receptor binding site" *Molecular Immunology* 25(8):705–711 (1988).
Baniyash et al., "Inhibition of IgE binding to mast cells and basophils by monoclonal antibodies to murine IgE" *European Journal of Immunology* 14:799–807 (1984).
Burt et al., "Analysis of the interaction between rat immunoglobulin E and rat mast cells using anti–peptide antibodies" *Molecular Immunology* 24(4):379–389 (1987).
Burt et al., "Inhibition of binding rat Ige to rat mast cells by synthetic IgE peptides" *European Journal of Immunology* 17:437–440 (1987).

Conrad et al., "The interaction of human and rodent Ige with the human basophil IgE receptor" *J. of Immunology* 130(1):3273–333 (1983).
Conrad, D.H., "FcεRII/CD23: The low affinity receptor for IgE" *Ann. Rev. Immunol.* 8:623–645 (1990).
Disenhofer, "Crystallographic refinement and atomic models of a human Fc fragment and its complex with fragment of protein a from *Staphylococcus aureus* at 2.9– and 2.8–A resolution" *Biochemistry* 20(9):2361–2370 (1981).
Geha et al., "IgE sites relevant for binding to type 1 Fc ε (FCER) receptors on mast cells" *J. Allergy & Clin. Immunol.* (abstract) 79(1):129 (1987).
Hakimi et al., "The α subunit of the human IgE receptor (FcERI) is sufficient for high affinity IgE binding" *Journal of Biological Chemistry* 265(3):22079–22081 (1990).
Helm et al., "Blocking of passive sensitization of human mast cells and basophil granulocytes with IgE antibodies by a reconbinant human ε chain fragment of 76 amino acids" *Proc. Natl. Acad. Sci.* 86:9465–9469 (1989).
Helm et al., "The mast cell binding site on human immunoglobulin E" *Nature* 331:180–183 (1988).
Hoffman, D.R., "Enzyme–linked immunosorbent assays (ELISA) for immunoglobulin E and blocking antibodies" *Methods in Enzymology,* Chapter 45, 73:656–666 (1981).
Ishizaka, K., "Immunoglobulin E (IgE)" *Methods in Enzymology* 116 (Part II):76–94 (1985).
Kinet et al., "How Antibodies Work: Focus on Fc Receptor" *FASEB J.* 2(1):14–17 (1988).
Kulczycki et al., "The interaction of IgE with rat basophilic leukemia cells I. Evidence for specific binding of Ige" *Journal of Experimental Medicine* 139:600–616 (1974).
Kurokawa et al., "Expression of human immunoglobulin ε chain cDNA om *E coli*" *Nucleic Acids Research* 11(10):3077–3085 (1983).
Liu et al., "Expression of a biologically active fragment of human IgE ε chain in *Escherichia coli*" *Proc. Natl. Acad. Sci.* 81:5369–5373 (1984).
Metzger et al., "How Antibodies work: focus on Fc receptors" *FASEB J.* 2(1):3–11 (1988).

(List continued on next page.)

*Primary Examiner*—Christina Y. Chan
*Assistant Examiner*—Patrick J. Nolan
*Attorney, Agent, or Firm*—Craig G. Svoboda

[57] ABSTRACT

Two classes of polypeptides derived from human IgE are described. One class binds selectively to the high affinity IgE receptor on mast cells and basophils, but not to the low affinity IgE receptor on B-cells, monocytes, eosinophils and platelets. The other class binds to the low affinity receptor, but not the high affinity receptor. The differential binding polypeptides of this invention are useful in diagnostic procedures for IgE receptors or in the therapy of IgE-mediated disorders such as allergies. They also are useful in preparing antibodies capable of binding regions of IgE that participate in receptor binding.

26 Claims, 1 Drawing Sheet

OTHER PUBLICATIONS

Neurath, A.R., "Use of $^{125}$I–labeled anti–2,4–dinitrophenyl (DNP) antibodies as a general tracer in solid–phase radioimmunoassays" *Methods in Enzymology* 73:127–138 (1981).

Nio et al., "Inhibitionof histamine release by synthetic human IgE peptide fragments: structure–activity studies" *Peptide Chemistry* pp. 203–208 (1989).

Nissim et al., "Mapping of the high affinity Fc ε receptor binding site to the third constant region domain of IgE" *EMBO Journal* 10(1):101–107 (Jan. 1991).

Nitta et al., "Preliminary trial of specific targeting therapy against malignant glioma" *Lancet* 335(8686):368–371 (Feb. 17, 1990).

Padlan et al., "A model of the Fc of immunoglobulin E" *Molecular Immunology* 23(10):1063–1075 (1986).

Riske et al., "High affinity human IgE receptor (Fc & RI). Analysis of functional domains of the α–subunit with monoclonal antibodies" *Journal of Biological Chemistry* 266(17):1124–1125 (Jun. 15, 1991).

Robertson et al., "IgE structure–function relationships defined by sequence directed antibodies induced by synthetic peptides" *Molecular Immunology* 25(2):103–113 (1988).

Schwarzbaum et al., "Mapping of murine IgE epitopes involved in IgE–Fcε receptor interactions" *European Journal of Immunology* 19:1015–1023 (1989).

Stanworth et al., "Synthetic peptides comprising sequences of the human immunoglobulin E heavy chain capable of releasing histamine" *Biochemical Journal* 180(3):665–668 (1979).

Stanworth et al., "The use of synthetic peptides in the delineation of immunoglobulin antigenic epitopes and Fc effectorfunctions" *CIBA Found. Symp.* 119:226–244 (1986).

Tung, A.S., "Production, purification, and characterization of antigen–specific murine monoclonal antibodies of IgE class" *Methods in Enzymology,* Chapter 6, 92:47–66 (1983).

Vercelli et al., "The B–cell binding site on human immunoglobulin E" *Nature* 338:649–651 (1989).

Weetall et al., "Mapping the site of interaction between murine IgE and its high affinity receptor with chimeric Ig" *J–Immunol* 145(11):3849–3854 (Dec. 1, 1990).

Kabat, Sequences of Proteins of Immunological Interest 5$^{th}$ Edition, vol. 1, pp. 662–663, 689–690, 1991.

```
         β-strand A           loop AB         β-strand B
360  XDSNPRGVSAYLSRPSPFDXLFIRKSPTIT
                            1,7              8 loop BC      β-strand C       loop CD
390  CLVVDLAPSKGTVNLTWSRXASXXGKPVNH
            2              9                3

β-strand D    loop DE       β-strand E        loop EF
420  STRKEEKQRXNXXGTLTVTSTLPVGTRDWI
           6                    10                4

β-strand F    loop FG    β-strand G
450  EGETYQCRVTHPHLPRALXMRSTTKTSGP
          11                  5        12
```

FIG. 1

IMMUNOGLOBULIN VARIANTS

CROSS REFERENCE TO RELATED APPLICATIONS

The present application is a continuation under 37 C.F.R. § 1.60 of U.S. Ser. No. 08/328,596, filed Oct. 25, 1994, now abandoned; which is a file wrapper continuation under 37 C.F.R. § 1.62 of U.S. Ser. No. 08/178,583, filed Jan. 7, 1994, now abandoned; which is a file wrapper continuation under 37 C.F.R. § 1.62 of U.S. Ser. No. 07/744,768, filed Aug. 14, 1991, now abandoned.

BACKGROUND OF THE INVENTION

This invention relates to polypeptides containing IgE sequences, especially IgE antagonists and to polypeptides capable of differential binding to FcεRI and FcεRII.

IgE is a member of the immunoglobulin family that mediates allergic responses such as asthma, food allergies, type 1 hypersensitivity and the familiar sinus inflammation suffered on a widespread basis. IgE is secreted by, and expressed on the surface of, B-cells. IgE synthesized by B-cells is anchored in the B-cell membrane by a transmembrane domain linked to the mature IgE sequence by a short membrane binding region. IgE also is bound to B-cells (and monocytes, eosinophils and platelets) through its Fc region to a low affinity IgE receptor (FcεRII, hereafter "FCEL"). Upon exposure of a mammal an allergen B-cells are clonally amplified which synthesize IgE that binds the allergen. This IgE in turn is released into the circulation by the B-cells where it is bound by B-cells (through the FCEL) and by mast cells and basophils through the so-called high affinity receptor (FcεRI, hereinafter "FCEH") found on the surface of the mast cells and basophils. Such mast cells and basophils are thereby sensitized for allergen. The next exposure to the allergen cross-links the FcεRII-bound IgE on these cells and thus activates their release of histamine and other factors which are responsible for clinical hypersensitivity and anaphylaxis.

The art has reported antibodies capable of binding to FCEL-bound IgE but not IgE located on FCEH (see for example WO 89/00138 and U.S. Pat. No. 4,940,782). These antibodies are disclosed to be clinically advantageous because they bind to IgE found on B-cells or circulating free in the body, but do not bind to FCEH and thus will not activate mast cells or basophils.

It is generally understood that FCEH, like FCEL, binds to a recognition site in the IgE constant (Fc) domain. The IgE recognition sites for the two receptors are poorly defined, despite considerable effort in the past directed to the problem.

Over the past decade several studies have been undertaken to determine which portion of the IgE molecule is involved in binding to FcεRI and FcεRII. Essentially three approaches have been tried. First, peptides corresponding to specific portions of IgE sequence have been used as either competitive inhibitors of IgE-receptor binding (Burt et al., *Eur. J. Immun.* 17:437–440 [1987]; Helm et al., *Nature* 331:180–183 [1988]; Helm et al., *Proc. Natl. Acad. Sci.* 86:9465–9469 [1989]; Vercelli et al., *Nature* 338:649–651 [1989]; Nio et al., *Peptide Chemistry* p203–208 [1990]) or to elicit anti-IgE antibodies which would block IgE-receptor interaction (Burt et al., *Molec. Immun.* 24:379–389 [1987]; Robertson et al., *Molec. Immun.* 25:103–113 [1988]; Baniyash et al., *Molec. Immun.* 25:705–711 [1988]). For competitive peptides, the best that could be achieved was a sequence that was 1000-fold less active than IgE (Burt et al., *Eur. J. Immun.* 17:437–440 [1987]).

Helm et al., *Proc. Natl. Acad. Sci.*, 86:9465–9469 (1989) found that a peptide corresponding to residues 329–409 blocked in vivo sensitization of human basophil granulocytes with human IgE antibodies. Further studies indicated that residues 395–409 were not essential for binding of the 329–409 peptide to FcεRI (Helm et al., *Proc. Natl. Acad Sci.* 86:9465–9469 [1989]). Note that the IgE described below had the sequence of Padlan et al., *Mol. Immun.*, 23:1063 (1986), but that the IgE residue numbers used herein are those of Kabat et al. *Sequences of Proteins of Immunological Interest* (National Institutes of Health, Bethesda, Md. 1987).

Vercelli et al., *Nature*, 338:649–651 (1989) used recombinant IgE peptides as well as anti-Fcε monoclonal antibodies to investigate the B-cell (FcεRII) binding site of human IgE. They concluded that the FcεRII binding site is in FCε3 near K399-V402.

Burt et al., *Eur. J. Immun.*, 17:437–440 (1987) investigated seven peptides for competition against rat IgE in binding to rat mast cells. Their most active peptide, p129, was 1000-fold less active than IgE. p129 corresponds to human sequence 439–453 which includes loop EF. Another of their peptides, p130, corresponding to residues 396–419 in the Fcε3 domain, had no activity.

Robertson et al., *Molec. Immun.*, 25:103–113 (1988) assessed IgE binding by sequence-directed antibodies induced by several synthetic peptides. They concluded that the sequence defined by their ε-peptide-4 (corresponding to residues 446–460), were not significantly involved in receptor binding while the sequence defined by their ε-peptide-3 (corresponding to residues 387–401), was likely to be proximal to the IgE-receptor recognition site.

Nio et al., *Peptide Chemistry*, p203–208 (1990) evaluated numerous peptides with respect to their ability to inhibit histamine release by human basophils in vitro. Only one peptide (peptide 2, Table 1), exhibited specific inhibition; this peptide encompassed residues 376–388. However, a larger peptide which incorporated this sequence (peptide 3, Table 1), had no inhibitory activity.

Second, mutations in IgE have been partially explored. Schwarzbaum et al., *Eur. J. Immun.*, 19:1015–1023 [1989] (supra) found that a point mutant P404H (P442H herein) had 2-fold reduced affinity for FcεRI on rat basophilic leukemia (RBL) cells, but the interpretation of this finding is controversial (Weetall et al., *J. Immunol.*, 145, 3849–3854 [1990]).

Third, chimeric molecules have been constructed. Human IgE does not bind to the murine receptor (Kulczycki Jr., et al., *J. Exp. Med.*, 139:600–616 [1974]) while rodent IgE binds to the human receptor with a reduced affinity (Conrad, et al., *J. Immun.*, 130:327–333 [1983]); human IgG1 does not bind to IgE receptors (Weetall et al., *J. Immun.*, 145:3849–3854 [1990]). Based on these observations, several groups have constructed human-murine chimeras or human IgE-IgG chimeras. Weetall et al., *J. Immun.*, 145:3849–3854 (1990) made a series of human IgG1-murine IgE chimeras and concluded that the Fcε2 and Fcε3 domains are involved in binding murine FcεRI while the Fcε4 domain is unlikely to be involved in binding to murine FcεRI (but may possibly be involved in binding to FcεRII). However, their conclusions rest primarily on lack of binding by chimeras and since three of their five chimeras lacked some interchain disulfide bonds, the conclusions drawn from these data are uncertain.

Nissim et al., *EMBO J.*, 10:101–107 (1991) constructed a series of human-murine IgE chimeras and measured binding to RBL cells. Their study included chimeras which incorporated receptor binding into molecules which should otherwise not bind. They concluded that the entire binding site of IgE which binds with high affinity to the specialized Fcε receptor on RBL cells could be assigned to Fcε3.

The results reported by these authors (e.g. Helm et al., and Burt et al.,) are inconsistent. Further, in the case of anti-IgE antibodies it is difficult to eliminate the possibility of non-specific blocking due to steric hindrance (Schwarzbaum et al., *Eur. J. Immun.* 19:1015–1023 [1989]). It is apparent that considerable confusion exists in the art as to the domains of IgE Fc which are involved in the binding of IgE to FCEH or in the maintenance of IgE conformation responsible for IgE binding to FCEH.

It is an object of this invention to identify polypeptides capable of differential binding to FCEL and FCEH.

It is an object herein to determine an IgE domain which is implicated in FCEH receptor binding, but which is not involved in FCEL receptor binding, and vice-versa.

It is another object herein to identify antagonists which are capable of inhibiting allergic responses, including antagonists that neutralize the FCEH or FCEL receptor-binding domains of Fcε and immunoglobulin analogues that bind FCEL but do not bind FCEH, or that bind FCEH but not FCEL.

It is another object to provide novel polypeptides for use in the assay of Fcε receptors and for use as immunogens or for selecting anti-IgE antibodies.

SUMMARY OF THE INVENTION

We have identified the domains of IgE which play an important role in binding IgE to its FCEL and FCEH receptors, and based on this information we have designed polypeptides which remain capable of substantially binding to only one of these two receptors while being substantially incapable of binding to the other of the receptors. These polypeptides are referred to as differential binding polypeptides. In particular, differential binding polypeptides that bind FCEL comprise IgE sequences in which the β-strand D domain is mutagenized, while FCEH-binding polypeptides comprise IgE sequences in which loop AB and/or β-strand B sequences are varied. Conversely, included herein are polypeptides comprising the IgE β-strand D domain, (but no functional loop AB-β strand B domain), bind differentially to FCEH, while polypeptides comprising the IgE loop AB-β-strand B domain but no functional β-strand D domain) bind differentially to FCEL.

The differential binding polypeptides of this invention are sufficiently homologous with the amino acid sequence of an IgE heavy chain that they retain the capability to bind FCEL or FCEH, but are varied such that they no longer retain the ability to bind to both receptors. In various embodiments, the polypeptides of this invention additionally comprise amino acid sequences obtained from IgE or other immunoglobulins, cytotoxic substances, detectable labels or conformation-restraining groups.

The differential binding polypeptides of this invention are useful in diagnostic procedures for IgE receptors or in the therapy of IgE-mediated disorders such as allergies. They also are useful in preparing antibodies capable of binding regions of IgE that participate in receptor binding.

BRIEF DESCRIPTION OF THE FIGURE

FIG. 1 depicts the sequence of human IgE Fcε2 and Fcε3 (SEQ. ID. 1). This particular sequence is from Padlan et al., *Molec. Immun.*, 23:1063–1075 (1986). Residues are numbered according to Kabat (supra). "X" residues are included to align the Padlan IgE sequence with the Kabat numbering scheme. Sequences which were altered in preparing various IgE mutants are underlined; bold numbers below the lines denote the mutant number. β-strand residues are overlined; loop residues are defined by all residues intervening between two β-strands.

DETAILED DESCRIPTION OF THE INVENTION

The polypeptides of this invention contain an amino acid sequence which is homologous to that of a naturally occurring IgE and have the ability to bind specifically and differentially to FCEL or FCEH. The degree of homology is not critical since only enough IgE sequence needs to be retained to enable the IgE to bind specifically to one of the two receptors. In general, the polypeptides of this invention will be about from 80% to 99% homologous with a polypeptide sequence of a naturally occuring IgE heavy chain Fc region. Homology is determined by conventional methods in which all substitutions are considered to be nonhomologous (whether conservative or nonconservative) and in which the sequences are aligned to achieve maximal homology.

It will be understood that the residue numbers referred to herein are those of Kabat, and that these numbers in most instances will not correspond to the residue numbers of a candidate IgE or fragment thereof. It will be necessary to compare the entire candidate sequence with the FIG. 1 sequence in order to align the residues and correlate the residue numbers. In addition, the identity of certain individual residues at any given Kabat site number may vary from IgE to IgE due to interspecies or allelic divergence. When for example it is stated that substitutions are introduced at residue R383 (human IgE) it will be understood that this includes introducing a substitution at the same site in another animal species or human IgE allele or other naturally occuring sequence variant even though this same site in loop AB of such other IgEs may be located at a different residue number or may be a different residue. However, for the sake of clarity and simplicity the residue numbers and identities of the Kabat human IgE heavy chain sequences generally will be used herein (unless the residue is deleted in the Padlan sequence, in which case the Kabat number will be referred to with the residue designated "X").

The differential binding polypeptides of this invention typically contain about from 5 to 250 residues which are homologous to an IgE heavy chain Fc region, but ordinarily will contain about from 10 to 100 such residues. Usually, the IgE Fc3 and Fc4 regions will be present, with the Fc3 domain providing residues directly involved in receptor binding with Fc4 being present to ensure comformational integrity.

Generally, the IgE is human IgE, although animal IgE such as rat, murine, equine, bovine, feline or porcine IgE is included. As noted above, there will be variation in the residue identities and numbers for these IgEs compared to the FIG. 1 sequence.

FCEH and FCEL are respectively defined to be the high affinity IgE receptor (FCεRI, Ishizaka et al., *Immunochemistry*, 7:687–702 [1973]) found on mast cells or basophils, and the low affinity receptor (FCεRII, or CD23) found on cells involved in inflammation such as monocytes, eosinophils and platelets, as well as B-cells (Capron et al., *Immun. Today*, 7:15–18 [1986]). FCEH and FCEL include alleles and predetermined amino acid sequence variants thereof which bind IgE. While FCEH contains several polypeptide chains binding to its alpha chain is all that need be assayed since the alpha chain is the portion of FCEH which binds IgE.

Differential binding means that the polypeptide will bind to FCEL or FCEH to the extent of at least about 75% of the degree with which the homologous native IgE binds to that receptor, but will not bind to the other receptor to more than about 20% of the degree that the homologous IgE binds to the other receptor. Included within this invention are polypeptides that are capable of binding to one of the two receptors to a greater degree than native IgE. The degree of binding is determined in the fashion set forth in Example 2 below.

FCEL-Specific Polypeptides

These polypeptides bind preferentially to the low affinity receptor. The preferred embodiment is mutant 6 (table 3), in which the substitution of 4 residues within the human IgE heavy chain sequence K423-R428 substantially abolished FCEH binding. However, it will be understood that many other related IgE sequence variants are capable of differential binding to the FCEL receptor. These variants typically will contain Fcε3 sequences in which residues within the β-strand D domain have been substituted or deleted, and/or an additional residue inserted adjacent to one of such β-strand D domain residues. The beta strand D domain also includes from 1 to 3 residues N- or C-terminal to the beta strand D residues T421-R428 (FIG. 1), and therefore extends from N418-X431 (FIG. 1, wherein X indicates a residue omitted from U266 IgE but found in the Kabat sequence). Those skilled in the art will be able to routinely screen for FCEL-specific polypeptides using the methods shown in the examples once it is understood that the beta-strand D domain is the site which is targeted for mutagenesis.

The preferred FCEL-specific polypeptide is one in which a residue has been substituted or deleted from within the β-strand D domain. Four residues were substituted in generating mutation 6, and any one or more of these substitutions may be responsible for the loss in FCEH binding while retaining FCEL binding. In general, substitutions will be nonconservative, i.e., substituted residues generally will differ substantially from those found within the homologous native IgE in terms of charge, hydrophobicity or bulk. In general, a maximum of 4 of β-strand domain residues are varied (and are usually residues 423, 424, 426 and/or 428), although typically any 1 to 5 of these residues are suitable for variation. In general, no more than 4 residues need to be varied and optimally only one will be varied.

K423 and/or K426 are substituted with any of a residue selected from the group of Arg, His, Cys, Met, Phe, Tyr, Trp, Pro, Gly, Ala, Val, Ile, Leu, Ser, Thr, Asp, Glu, Gln and Asn, preferably Gly, Pro, Glu, Gln and Asp and most preferably Pro or Gln.

E424 and/or E425 are substituted with any of a residue selected from Asp, Asn, Gln, His, Lys, Arg, Cys, Met, Phe, Tyr, Trp, Pro, Gly, Ala, Val, Leu, Ile, Ser and Thr, preferably Arg, Lys, Pro, Gly and His and most preferably Arg.

R428 and/or R422 are substituted with Cys, Met, Phe, Tyr, Trp, Pro, Gly, Ala, Val, Leu, Ile, Ser, Thr, Asp, Glu, Asn, Gln, His, and Lys, preferably Cys, Met, Phe, Tyr, Trp, Pro, Gly, Ala, Val, Leu, Ile, Ser, Thr, Asp, Glu, Asn and Gln, and most preferably Tyr.

T421 is substituted with Cys, Met, Phe, Tyr, Trp, Pro, Gly, Ala, Val, Len, Ile, Ser, Asp, Glu, Asn, Gln, His and Lys, preferably Met, Phe, Tyr, Trp, Pro, Gly, Ala, Val, Leu, Ile, Asp, Glu, Asn, Gln, His and Lys, and most preferably Phe, Trp, Pro, Gly, Ala, Val, Len and Ile.

S420 is substituted with Met, Phe, Tyr, Trp, Pry, Gly, Ala, Val, Leu and Ile, and preferably Pro or Gly.

X429 is substituted with any other naturally occuring amino acid residue.

It is likely that optimal differential and FCEL binding activity will be achieved by a combination of mutations. Preferably, FCEH binding will be less than 10% of native homologous IgE, and optionally will range from undetectable to 3% of native homologous IgE, while FCEL binding ranges from at least about 75% of native homologous IgE to 90%, and preferably 95% to 125%. The mutations should be as conservative as possible, i.e., involve as modest changes in hydrophobicity, charge or bulk as possible, yet still result in a polypeptide exhibiting these differential binding characteristics.

Any one or more of the β-strand D domain residues also may be deleted. Deletion of residues may possess the advantage of not introducing potentially immunogenic sites into the IgE analogue.

Examples of candidate β-strand D domain substitutional or deletional variants are set forth in the following table 1a. To determine the sequence of each variant, identify the residue for each variant number under each site. For example, the sequence of compound 19 comprises C388 E389 E390, etc.

TABLE 1a

| | \multicolumn{6}{c}{HuIgE Site} | | | | |
|---|---|---|---|---|---|---|
| AA[1] | 423 K | 424 E | 425 E | 426 K | 427 Q | 428 R |
| C | 19 | 20 | | 37 | | 55 |
| M | 18 | 21 | | 38 | | 56 |
| F | 8, 80 | 22 | | 39 | | 57, 88 |
| Y | 7 | 23 | | 40 | | 4, 75, 83–84, 89, 97 |
| W | 6 | 24 | | 41 | | 58, 85 |
| P | 1, 74, 78–79, 89, 103 | 25, 97 | | 42 | | 59 |
| G | 5, 76–77 | 26 | | 43 | | 60 |
| A | 12, 98–99 | 27, 98, 100 | | 44, 98, 101 | | 61, 98, 102 |
| V | 13, 97 | 28 | | 45 | | 62 |
| L | 14, 81 | 29 | | 46 | | 63 |
| I | 15, 82 | 30 | | 47 | | 64 |
| S | 16 | 31 | | 48 | | 65, 103 |
| T | 17 | 32 | | 49 | | 66, 104, 105 |

TABLE 1a-continued

| | HuIgE Site | | | | | |
|---|---|---|---|---|---|---|
| AA[1] | 423 K | 424 E | 425 E | 426 K | 427 Q | 428 R |
| D | 9 | | 79 | 50 | | 67, 68 |
| E | 9, 94 | 1, 3–19, 37–54 75, 88, 89, 90–93, 99, 101, 102, 105 | 1–72, 74, 55–72, 93–94, 99, 100–105 | 51 76–78, 80–88, | | 68, 87 |
| N | 10 | 33 | | 52, 79, 84 | 79 | 69 |
| Q | 11 | 34 | | 3, 54, 75, 80, 82–83, 85–89, 103–104 | 1–72, 75, 77, 78, 80–95, 97–103, 105 | 70 |
| H | 83, 104 | 35, 78, 84 | | 53 | | 71 |
| K | 2–4, 20–72, 75, 85–88, 91–93, 100–102, 105 | 36, 77, 79, 94 | | 1–2, 5–36, 55–72, 74, 76, 77–90, 91, 93–95, 97, 99, 100, 102, 105 | 104 | 72, 79 |
| R | 84 | 2, 74, 76, 80, 81, 83, 85–87, 103–104 | 89 | | | 1–3, 5–54, 74, 76–78, 80–82, 90–92, 94, 99, 100–101 |
| Δ[2] | 90, 95, 96 | 91, 95, 96 | 91, 96 | 92, 96 | 96 | 93, 95, 96 |

[1]Amino acid residue substituted into the analogue
[2]Signifies a deletion

Insertion of one or more extraneous residues adjacent to a residue within the β-strand domain also falls within the scope of this invention. Typically, only one residue will be inserted, although from 2 to 4 or more residues can be inserted adjacent to any one site within the domain. Smaller numbers of inserted residues will be preferred in order to avoid the introduction of immunogenic sites. This, however, is merely a matter of choice. In general, insertions will be made at a single site, although insertions can be made adjacent to any two or more β-strand D domain residues.

Insertions typically are made between the following residues: 422 and 423, 423 and 424, 424 and 425, 425 and 426, 426 and 427, 427 and 428 and/or 428 and 429. The inserted residue or residues generally will exhibit charge, bulk or hydrophobicity character which is distinct from that of the flanking residues. For example, candidate insertions can be selected from the following table 2a.

TABLE 2a

| Insertion | β-strand D domain site[1] |
|---|---|
| Q | 1, 2, 3, 4, 5, 7 or 8 |
| D | 1, 2, 3, 4, 5, 6 or 7 |
| E | 1, 2, 3, 4, 5, 6 or 7 |
| F | 1, 2, 3, 4, 5, 6 or 7 |
| W | 1, 2, 3, 4, 5, 6 or 7 |
| P | 1 or 2 |
| K | 2 or 3 |
| R | 2 or 3 |
| EK | 2 or 7 |
| ER | 2 or 7 |
| DK | 2 or 7 |
| DR | 2 or 7 |
| G | 1 or 2 |
| A | 8 |
| Y | 6 or 7 |
| N | 1, 2, 3, 4, 5, 7 or 8 |
| H | 1, 2, 3, 4, 5, 7 or 8 |

TABLE 2a-continued

| Insertion | β-strand D domain site[1] |
|---|---|
| I | 1, 2, 3, 4, 5, 7 or 8 |

[1]422R - site 1 - 423K - site 2 - 424E - site 3 - 3425E - site 4 - 426K - site 5 - 427Q - site 6 - 428R - site 7 - 429X y - site 8. Absence of a site indicates no insertion at that site.

In general, a maximum of 4 of the 14 β-strand D domain residues are varied (and are usually residues 423, 424, 426 and/or 428), although typically any 1 to 5 of these residues are suitable for variation. In general, no more than 4 residues need to be varied and optimally only one will be varied.

The FCEL-specific polypeptides need only contain so much of the IgE Fcε AB-B domain sequence as is required to substantially maintain FCEL binding. This is readily determinable by preparing polypeptides with the AB-B domain and increasing number of flanking residues, e.g., β-strand A (N-terminal) or loop BC, β-strand C, loop CD, β-strand D (inactive), loop DE, β-strand F, loop F6, β-strand G, and Fcε4 (C-terminal). In general, the entire IgE sequence from Fcε3–Fcε4 is used, although fragments of FcE3 containing the AB-B domain may be satisfactory.

The FCEL-specific polypeptides are provided as linear or comformationally restrained polypeptides. The polypeptides are conformationally restrained by cross-linking the polypeptide, preferably at the N- and C-termini so as to produce a cyclic structure. In preferred embodiments the cyclic forms have the following structure:

Formula I

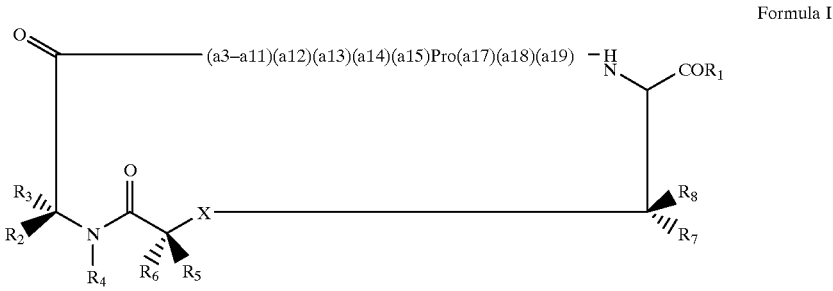

wherein (a3-a11) is a bond or the sequence -R373 -F381; a12 and a18 are hydrophobic amino acid residues; a13 and a14 are basic amino acid residues; and a15, a17 and a19 are hydrophilic amino acid residues;

$R_1$ is selected from
(a). hydroxy,
(b). $C_1$–$C_8$ alkoxy,
(C). $C_3$–$C_{12}$ alkenoxy,
(d). $C_6$–$C_{12}$ arlyoxy,
(e). acylamino-$C_1$–$C_8$-alkoxy
(f). pivaloyloxyethoxy,
(g). $C_6$–$C_{12}$ aryl-$C_1$–$C_8$-alkoxy where the aryl group is unsubstituted or substituted with one or more of the groups nitro, halo, $C_1$–$C_4$-alkoxy, and amino;
(h). hydroxy substituted $C_2$–$C_8$ substituted alkoxy; and
(i). dihydroxy substituted $C_3$–$C_8$ alkoxy;

$R_2,R_3,R_5,R_7,R_8$ are the same or different and are selected from
(a). hydrogen,
(b). $C_6$–$C_{12}$ aryl where the aryl group is unsubstituted or substituted by one or more of the groups nitro, hydroxy, halo, $C_1$–$C_8$ alkyl, halo-$C_1$–$C_8$ alkyl, $C_1$–$C_8$ alkoxy, amino, phenyl, acetamido, benzamido, di-$C_1$–$C_8$ alkylamino, $C_6$–$C_{12}$ aroyl, $C_1$–$C_8$ alkanoyl, and hydroxy substituted $C_1$–$C_8$ alkyl,
(c). $C_1$–$C_{12}$ normal, secondary, tertiary or $C_3$–$C_{12}$ cyclic saturated or unsaturated alkyl substituted with halo, $C_1$–$C_8$ alkoxy, $C_6$–$C_{12}$ aryloxy, hydroxy, amino, acetamido, $C_1$–$C_8$ alkylamino, carboxy or carboxamide;

$R_2$ and $R_3,R_5$ and $R_6$, or $R_7$ and $R_8$ may optionally and independently be joined together to form a carbocyclic or heterocyclic ring of from four to seven atoms where the heteroatoms are selected from O, S, or $NR_{10}$ where $R_{10}$ is selected from hydrogen, $C_1$–$C_8$-alkyl, $C_2$–$C_8$-alkenyl, $C_6$–$C_{12}$-aryl, $C_6$–$C_{12}$-aryl-$C_1$–$C_8$-alkyl, $C_1$–$C_8$-alkanoyl, and $C_6$–$C_{12}$ aroyl, $R_4$ is selected from hydrogen, $C_1$–$C_8$-alkyl, $C_2$–$C_8$-alkenyl, $C_6$–$C_{12}$-aryl, $C_6$–$C_{12}$-aryl-$C_1$–$C_8$-alkyl, $C_1$–$C_8$-alkanoyl, and $C_6$–$C_{12}$ aroyl;

$R_2$ or $R_3$ may be optionally joined with $R_4$ to form a piperidine, pyrrolidine or thiazolidine ring;

X is selected from an O or S atom,
$NR_9$ wherein $R_9$ is hydrogen, $C_1$–$C_8$-alkyl, $C_3$–$C_8$-alkenyl, $C_6$–$C_{12}$-aryl, $C_6$–$C_{12}$-aryl-$C_1$–$C_8$-alkyl, $C_1$–$C_8$-alkanoyl, and $C_6$–$C_{12}$ aroyl
$C_6$–$C_{12}$ aryl,
$C_1$–$C_8$ alkanoyl, and
$(CH_2)k$ where k is an integer from 0 to 5; and pharmaceutically acceptable salts thereof.

As used herein and unless specified otherwise: alkyl and alkenyl denote straight and branched hydrocarbon chains having single or double bonds, respectively; $C_6$–$C_{12}$ aryl groups denote unsubstituted aromatic rings or fused aromatic rings such as, for example, phenyl or naphthyl; halo denotes F, Cl, Br, or I atoms; alkoxy denotes an alkyl group bonded through O to the indicated site. Examples of $C_1$–$C_8$ alkyl or $C_2$–$C_8$ alkenyl groups include methyl, ethyl, propyl, isopropyl, butyl, t-butyl, pentyl, isopentyl, hexyl, vinyl, allyl, butenyl and the like; examples of $C_3$–$C_{10}$-cycloalkyl groups include cyclopropyl, cyclopentyl, cyclohexyl, and the like; heterocyclic rings include but are not limited to pyridyl, thienyl, furyl, indolyl, benzthienyl, imidazolyl, thiazolyl, quinolinyl and isoguinolinyl. Hydrophobic amino acid residues include naturally occurring or synthetic residues having hydrophobic side chains, e.g. Phe, Leu, Ile, Val, Norleu, and the like. Hydrophilic amino acid residues include naturally occurring or synthetic residues having charged or uncharged hydrophilic side chains, e.g. ornithine, Ser, Thr, Tyr, His, Asp, Glu, Lys and Arg. Preferably a15, a17 and a19 are unchanged and bear normal, secondary or tertiary mono or di-hydroxy substituted alkyl side chains. Basic residues have guanidino or amino-substituted side chains for the most part.

8 murine monoclonal antibodies, designated MA10, MAE11, MAE12, MAE13, MAE14, MAE15, MAE16 and MAE17, were prepared by immunizing mice with human IgE and screening for anti-IgE activity. They are useful in identifying IgE amino acid sequence variants in which the FCEH-binding domain has been modified. Candidate polypeptides are incubated with these antibodies, and analogues to which these antibodies fail to bind are selected for further evaluation, e.g., determination of their FCEH and FCEL receptor binding characteristics. Any antibody, whether of murine, human, or another animal species in origin (or CDR grafted onto a human immunoglobulin), which has the epitopic specificity of any of antibodies MAE10–MAE17 (especially MAE11, MAE13 or MAE17) will be equally acceptable. Such antibodies are easily identified by immunizing a suitable animal with IgE of the appropriate animal origin and screening the products for antibodies having the ability to compete for IgE with these antibodies or those which map to substantially the same epitopic site(s) as MAE10–MAE17. MAE11 and MAE13 recognize different epitopes. MAE17 was most effective in suppressing B-cell IgE synthesis despite the fact that MAE11 and MAE13 exhibited greater IgE affinity. This was attributed to its ability to complement (IgG2a containing effector Fc). MAE13 and MAE17 bound to IgE with the greatest affinities. In addition, each of the MAE10–MAE17 antibodies bound to B-cell cell surface IgE (membrane-bound IgE, not FCEL-bound IgE). Accordingly, each of these antibodies (or their monovalent forms such as Fab or Fab') will be useful in the treatment of allergies. In further embodiments, appropriate CDR and framework residues from these antibodies (particularly the high affinity antibodies MAE13 or MAE17) are substituted into the variable region of a human immunoglobulin in order to provide immunoglobulins which are more suitable for the therapy of human allergies. Such humanized antibodies are made using CDR/framework grafting procedures that are conventional per se. In light of our experience with MAE17, it would be preferable to use a human IgG2 (or other complement fixing antibody) as the recipient immunoglobulin for CDR/framework grafting. This antibody also can be used in the monovalent form, e.g., as Fab or Fab' fragments. Therefore MAE13 or MAE17 CDRs are grafted onto a human IgG which contains an effector Fc domain.

The AB-B domain-containing, FCEL-specific polypeptides of this invention optionally are associated with other substances or are fused to additional polypeptide sequences. The polypeptides generally contain only IgE-homologous sequences, although they also may be fused to other polypeptides such as cytotoxic or immunosuppressive polypeptides. Cytotoxic polypeptides include IgG Fc effector sequences and polypeptide toxins such as diphtheria toxin or ricin A chain (U.S. Pat. Nos. 4,714,749 and 4,861,579). A preferred fusion is one in which the FCEL-specific sequence (such as that of the Fcε3–Fcε4 sequence of mutant 6) is fused at its N-terminus (i.e., at approximately D360) to the C-terminus of an immunoglobulin, or an immunoglobulin fragment terminating at the C-terminus of IgG Fcγ2 or IgG Fcγ3. The immunoglobulin sequences fused to the FCEL-specific polypeptides herein include Fc or variable sequences of the heavy chains of IgG1, IgG2, IgG3, IgG4, IgE, IgM, IgD or IgA. Any FCEL-specific heavy chain fusion optionally is disulfide bonded in the ordinary fashion to heavy chains having the same sequence (thereby forming homodimers) or to different heavy chains (therby forming heterodimers). Such different heavy chains include heavy chains which are not FCEL-specific, e.g., native IgE or other immunoglobulin heavy chains. In addition, the heavy chain hetero- or homodimers optionally are disulfide bonded to light chains in the fashion of native immunoglobulins.

In some embodiments, immunoglobulins comprising a FCEL-specific polypeptide will also comprise an immunoglobulin variable region. The antigenic specificity of the variable region is not critical. Suitable variable regions are those which are capable of binding haptens, or polypeptides or proteins from human, animal, plant, fungal, bacterial or insect sources. The specificity may be unknown or the variable region may have the ability to bind to a predetermined antigen. If the immunoglobulin is to have a functional variable domain it is preferred that it have a known antigenic specificity. Antigenic specificity may include the ability to bind antigens associated with a cytotoxic or immune response particularly lymphoid cell antigens such as CD3 or CD8, B-cell surface antigens, helper or suppressor cell surface antigens, or epitopes located in the variable region of effector subtypes of IgG. Alternatively, the immunoglobulin specificity is directed against the Fc region of effector subtypes of IgG, in this case however it being preferable that the FCEL-specific polypeptide not suppress complement binding or ADCC functions of the IgG.

In another embodiment, FCEL-specific polypeptides are covalently bound to a cytotoxic agent. For example, the polypeptide ricin D toxin isolated from the *Ricinus communis* plant can be bound to the carboxy terminus of the Fc domain, either by chemical means or, most preferably, by production of a fusion protein using standard recombinant DNA methods. This provides a means to selectively deliver the toxin only to cells expressing FCEL on their surfaces.

The FCEL-specific polypeptides need only contain so much of the IgE Fcε sequence as is required to substantially maintain FCEL binding. This is readily determinable by synthesizing or expressing the product and determining its activity. In general, the entire IgE sequence extending from Fcε2–Fcε4 can be used, although fragments containing only FcE3 and FcE4 are generally satisfactory.

In general the immunoglobulin sequences and the FCEL-specific sequence will be derived from the same species which is to be treated with the IgE analogue. Preferably, the immunoglobulin sequences are human.

The FCEL-specific polypeptides of this invention exclude the linear polypeptide sequences disclosed by Nio et al. (supra), as well as other prior art disclosing polypeptides which include the native IgE AB-B domain.

FCEH-Specific Polypeptides

These polypeptides are amino acid sequence variants of IgE or its fragments in which a residue within the AB-B domain has been deleted, substituted or another residue inserted so that the AB-B domain is no longer capable of binding to FCEL, and which contain sufficient beta strand D sequence to bind to the high affinity receptor. As disclosed above, the AB-B domain has been implicated in binding to FCEL since mutations in this domain have a serious impact on the binding of the IgE variants to the low affinity receptor. In particular, mutations in the C-terminal half of the AB loop and in the N-terminal half of beta strand B produce a divergence in IgE FCEL/FCEH specificity wherein the variant continues to bind to the high affinity receptor but largely fails to bind to the low affinity receptor. In addition, we have found that the IgE heavy chain beta strand D domain participates in binding to the high affinity receptor. Therefore, FCEH-specific differential binding polypeptides will comprise at least the FCEH-binding sequence of beta strand D and preferably also will contain a variant AB-B domain sequence that binds substantially only to FCEH.

In preferred embodiments amino acid sequence variation is introduced into the low affinity receptor binding functionality of the AB-B domain. Preferably, one or more of residues I382, R383, K384, S385, T387, I388, T389 and C390 are varied, although modifications can be introduced into loop AB N-terminal to these residues. Preferably, only one of R383, K384, S385, T387 or T-389 is mutated. When substituted at all, I382 and/or I388 generally are independently substituted with Asn, Gln, Leu, Val, His, Lys, Arg, Met, Phe, Tyr, Trp, Pro, Gly, Ala, Ser, Thr, Asp or Glu, preferably Trp, Pro, Gly, Ser, Thr, Asp or Glu. Ordinarily these two residues are not modified.

R383 typically is substituted with Cys, Met, Phe, Tyr, Trp, Pro, Gly, Ala, Val, Leu, Ile, Ser, Thr, Asp, Glu, Asn, Gln, His, or Lys, preferably Met, Phe, Tyr, Trp, Pro, Gly, Ala, Val, Leu, Ile, Ser, Thr, Asp, Glu, Asn or Gln and most preferably Ala, Glu, Asp or Ser.

K384 typically is substituted with Arg, His, Cys, Met, Phe, Tyr, Trp, Pro, Gly, Ala, Val, Ile, Leu, Ser, Thr, Asp, Glu, Gln and Asn, preferably Ala, Gly, Pro, Glu, Gln or Asp and most preferably Ala, Glu or Asp.

S385 is substituted with Asp, Asn, Gln, His, Lys, Arg, Cys, Met, Phe, Tyr, Trp, Pro, Gly, Ala, Val, Leu, Ile, Glu and Thr, preferably Ala, Tyr, Val, Ile, Leu, Phe, Arg, Lys and His and most preferably Ala, Val, Ile, Leu, Phe and Tyr.

When substituted, P386 usually is substituted by Gly, Ala, Cys, Val, Leu, Ile, Ser, Thr, Asp, Glu, Asn, Gln, His, Lys, Arg, Phe, Tyr, or Trp, and preferably Gly, Ala, Ser, Thr, Asp, Glu, Asn, Gln, His, Lys, Arg or Trp. Ordinarily, P386 is not modified.

T387 and/or T389 generally are independently substituted by Gly, Ala, Val, Leu, Ile, Ser, Asp, Pro, Glu, Asn, Gln, His, Lys, Arg, Cys, Phe, Tyr and Trp, preferably Gly, Ala, Val, Leu, Ile, Asp, Glu, Asn, Gln, His, Lys, Arg, Phe, Tyr and Trp, and most preferably Ala.

C390 ordinarily is not substituted except when employed as a component of a cyclizing group as shown in Formula I.

The differential FCEH-binding polypeptides of this invention will comprise the sequence of a functional FCEH-binding beta strand D domain. The beta strand D domain is defined above. In general, it is expected that the functional beta strand D domain need not contain all of the beta strand D domain residues, nor that it contain identical residues to those of the domain as set forth in FIG. 1. However, any modifications of the beta strand D domain residues will need to be conservative, if made at all, in order to preserve FCEH binding.

A particularly preferred embodiment of a FCEH-specific polypeptide is one which contains a beta strand D domain together with additional C-terminal sequence. The sequence of this embodiment extends from about T421 to about T440. Generally, the N-terminus of this embodiment is S420 or T421, while the C-terminus is T440, L441 or P442. In addition, one or more residues extraneous to this sequence are fused to its N- or C-termini. These extraneous residues are particularly useful in forming covalent or noncovalent bonds between the N- and C-termini of this polypeptide. The N- and/or C-termini preferably are covalently bonded through a side chain of a residue or through the polypeptide backbone. For example, cysteine residues are fused to the N- and C-termini and, upon oxidation, a polypeptide having a terminal disulfide bond is formed which joins the terminal ends of the polypeptide, thereby conformationally restraining the polypeptide. Alternatively, the alpha amino group of the polypeptide (or that of an extraneous N-terminally located residue) is covalently bonded to the sulfur atom of an extraneous C-terminally located cysteine residue to form thioether cyclic compounds analogous to those depicted in Formula I. Other cyclic compounds are prepared in the same fashion as described elsewhere herein. Also within the scope of this embodiment are amino acid sequence variants of native IgE sequences corresponding to the sequence of this embodiment. Beta strand D variants are selected to enhance binding to FCEH, while the sequence outside of the beta strand D domain need only retain sufficient conformational structure to properly juxtapose the N- and C-termini in substantially the same position as is the case with the native IgE sequence.

The FCEH-specific polypeptides herein optionally are covalently or noncovalently linked to accessory polypeptides (other immunoglobulin sequences, cytotoxic polypeptides and the like) in the same fashion as is described above for the FCEL-specific, AB-B domain-containing polypeptides. In addition, conformationally restrained (typically cyclic) polypeptides comprising the FCEH-binding sequence of the beta strand D domain are included within the scope hereof. Such polypeptides are identical to those shown in Formula I above except that the FCEH-binding beta strand D domain replaces the (a3)-(a19) moiety. Exemplary replacement moieties include S420-R428, T421-N430, S420-G433 and R422-R428 (note that sequences such as T421-N430 from U266 that omit a residue from the Kabat sequence can contain a residue at that site or may have a deletion at the same location, in the latter case here the Asn residue would occupy site 429).

Any one or more of the AB-B domain residues also may be deleted in order to substantially reduce or eliminate FCEL binding. Residue deletion may be preferred for the same reason noted above with respect to the beta strand D domain.

Examples of candidate AB-B domain substitutional or deletional variants are set forth in the following table 1b. To determine the sequence of each variant, identify the residue for each variant number under each site. For example, the sequence of compound 98 comprises A383 A384 A385, and represents the class of mutations to which mutant 7 belongs.

TABLE 1b

| AA[1] | 350 I | 351 R | 352 K | 353 S |
|---|---|---|---|---|
| C |  | 55 | 19 | 37 |
| M |  | 56 | 18 | 38 |
| F |  | 57, 88 | 8, 80 | 39 |
| Y |  | 4, 75, 83–84, 89, 97 | 7, 73 | 40 |
| W |  | 58, 85 | 6 | 41 |
| P |  | 59 | 1, 74, 78–79 | 42 |
| G |  | 60, 73 | 5, 76–77 | 43 |
| A |  | 61, 98, 102 | 12, 98–99 | 44, 98, 101 |
| V | 72 | 62 | 13, 97 | 45 |
| L | 73 | 63 | 14, 81 | 46 |
| I | 75 | 64 | 15, 82 | 47 |
| S |  | 65, 103 | 16 | 1–2, 5–36, 55–72, 74, 76–91, 93–95, 97, 99–100, 102, 105 |
| T |  | 66, 104, 105 | 17 | 49 |
| D |  | 67, 86 | 9 | 50 |
| E |  | 68, 87 | 89, 94 | 51 |
| N | 79 | 69 | 10 | 52, 79, 84 |
| Q | 1–71, 77, 78, 80–95, 97–103, | 70 | 11, 103 | 3, 54, 75, 80, 82–83, 85–89, 103–104 |
| H |  | 71 | 83, 104 | 4, 53 |
| K | 104 | 72, 79 | 2–4, 20–72, 75, 85–88, 91–93, 100–102, 105 | 48 |
| R |  | 1–3, 5–54, 74, 76–78, 80–82, 90–92, 94, 99–101 | 84 | 73 |
| A[2] | 96 | 93, 95, 96 | 90, 95, 96 | 92, 96 |

[1] Amino acid residue substituted into the analogue
[2] Signifies a deletion

Insertion of one or more extraneous residues adjacent to a residue within the AB-B domain also falls within the scope of this invention, although subsitutions or deletions are preferred. Typically, only one residue will be inserted, although from 2 to 4 or more residues can be inserted adjacent to any one site within the AB-B domain. Smaller numbers of inserted residues will be preferred in order to avoid the introduction of immunogenic sites. This, however, is merely a matter of choice. In general, insertions will be made at a single site, although insertions can be made adjacent to any two or more AB-B domain residues.

Insertions typically are made between the following residues: S385 and P386, P386 and T387, T387 and I388, and I388 and T389. The inserted residue or residues generally will exhibit charge, bulk or hydrophobicity character which is distinct from that of the flanking residues. For example, candidate insertions can be selected from the following table 2b.

TABLE 2b

| Insertion | AB-B domain site[1] |
|---|---|
| Q | 1, 2, 3, 4 or 5 |
| D | 1, 2, 3, 4 or 5 |
| E | 1, 2, 3, 4 or 5 |
| F | 1, 2, 3, 4 or 5 |
| W | 1, 2, 3, 4 or 5 |
| P | 1 or 2 |
| K | 2 or 3 |
| R | 2 or 3 |
| T | 3 or 4 |
| EK | 2 or 4 |
| ER | 2 or 4 |
| DK | 2 or 4 |
| DR | 2 or 4 |
| G | 1 or 2 |
| A | 5 |
| Y | 3 or 4 |
| N | 1, 2, 3, 4 or 5 |
| H | 1, 2, 3, 4 or 5 |
| I | 1, 2, 3, 4 or 5 |

[1]I382 - site 1 - R383 - site 2 - K384 - site 3 - S385 - site 4 - P386 - site 5 - T387. Absence of a site indicates no insertion at that site.

One or more of the AB-B domain residues are substituted or deleted, or additional residues inserted adjacent to such residues. In general, no more than 4 residues or sites are varied and optimally only one will be varied. Variations herein include combinations of insertions, deletions or substitutions. Excluded from the scope of FCEH specific polypeptides are the linear IgE polypeptide fragments disclosed by Nio et al. (or the naturally occuring sequence variants of such fragments, e.g. alleles and the like), together with any other such fragments disclosed by the prior art.

Therapeutic, Diagnostic and Preparatory Uses

The FCEH and FCEL-specific, differential binding polypeptides are useful for diagnostics and therapeutics. In in vitro diagnostic assays they are employed as specific binding reagents in assays for FCεRI or FCεRII, respectively. The polypeptides of this invention are labelled with a detectable substance such as an enzyme, fluorescent or chemiluminescent group, radioisotope or a specific binding moiety that binds to a detectable substance (such as an enzyme). A typical specific binding moiety is an immunoglobulin variable domain which is capable of binding to the detectable substance. FCEL and FCEH specific polypeptides comprising immunoglobulin variable domains are described in more detail above.

Assay systems that employ the polypeptides of this invention are analogous to the sandwich-type systems heretofore generally used in the immunoassay field. Here, the specfic polypeptide is employed in the same fashion as labelled antibodies directed against antigen (the FCEL or FCEH receptor) or as an absorption agent insolubilized on a matrix for the isolation of receptor from test sample. Redox, proteolytic, esterolytic or other conventional enzyme labels are conjugated to the polypeptides of this invention for use in conventional assay systems.

The differential binding polypeptides of this invention also are useful for the isolation of FCEL or FCEH from cell culture in preparing FCEL or FCEH for therapeutic or research purposes. The polypeptide is covalently bonded or noncovalently adsorbed to a matrix such as an ion exchange resin, an immunoaffinity column (containing an antibody capable of binding a polypeptide fused to the FCEH or FCEL-specific polypeptide), an immobilized antigen (where the FCEH or FCEL-specific polypeptide comprises an immunoglobulin variable region capable of binding to the antigen) or a cyanogen bromide activated polysaccharide. The immobilized FCEH or FCEL-specific polypeptide then is contacted with the receptor preparation under conditions such that the receptor is bound to the FCEH or FCEL-specific polypeptide. The receptor then is eluted by changing the pH or ionic conditions and separating the polypeptide preparation from the receptor.

The differential binding polypeptides herein are useful in preparing antibodies specific to the FCEH or FCEL-binding domain of IgE. For example, antibodies capable of binding specifically to the FCEH or FCEL-binding domains of IgE are selected by first immunizing a subject with IgE. Monoclonal antibodies then are selected in the ordinary way for native IgE binding, and the monoclonal antibodies then screened to identify those that bind to a FCEH or FCEL-specific polypeptide of this invention. Preferably the FCEH or FCEL-specific polypeptide will be identical in sequence to the corresponding sequence of the IgE used as immunogen except, of course, for the minimal mutations need to confer FCEH or FCEL differential binding specificity. For example, the IgE monoclonal antibodies can be selected for their inability to bind to mutation 6. If they are unable to bind to mutation 6 one can conclude that they bind to the FCEH-binding site and are therefore promising for use in diagnostic or therapeutic procedures that depend upon an antibody that fails to bind to FCEH-bound IgE but which binds to FCEL-bound IgE. Confirmation is obtained by determining that the antibody selected in fact binds to IgE bound to FCEL. Since the selected antibody is highly specific for the key site(s) involved in receptor binding it is then possible to reduce the size of the antibody; the bulk of the antibody is not needed for steric hinderance of the IgE-receptor interaction. Thus, it becomes feasible in allergy therapy to use anti-IgE monovalent antibodies or other anti-IgE fragments such as Fab, Fab' and the like.

Similarly, the FCEL or FCEH-specific polypeptides are useful as immunogens for raising antibodies capable of cross-reacting with native IgE only at epitopic sites outside of the domains varied in creating the FCEH or FCEL-specific polypeptides. For example, mutations 6 and 7 are useful for raising antibodies specific for IgE epitopes except for the mutated AB-B or beta strand B domains as the case may be.

The FCEH and FCEL-specific polypeptides are particularly useful in therapies for the treatment or prophylaxis of allergies, although the FCEH specific polypeptide subgroup which bears cytotoxic functionalities is not considered suitable for therapy since it could lead to degranulation of mast cells and basophils. Otherwise, the polypeptides typically are administered to a patient who is known to be sensitized to an allergen, preferably prior to an acute allergic response. The dosages and administration route will depend upon the accessory functionalities accompanying the polypeptides (e.g. cytotoxic agents, immunoglobulin effector functions, etc.), the condition of the patient (including the population of B cells or mast cells and basophils), the half-life of the polypeptide, the affinity of the polypeptide for its receptor and other parameters known to the clinician. As a general guide in the case of FCEH-specific polypeptide, one will determine from blood tests the amount of target cells circulating in the patient and determine the amount of polypeptide to displace or effectively compete with endogenous IgE taking into account the population of FCEH receptors as well as the half life and affinity of the polypeptide for FCEH. An excess of polypeptide calculated to be necessary to substantially displace native FCEH-bound IgE over a reasonable therapeutic interval will then be administered.

Therapeutic polypeptides are administered by intravenous intrapulmonary, intraperitoneal subcutaneous or other suitable routes. Preferably the polypeptides are administered s.c. or i.v. over a period of about from 1 to 14 days as required. In the case of FCEL-specific polypeptide one would determine the amount needed to inhibit, suppress or kill a substantial portion of the IgE-secreting B cell population. Inhibition or suppression of the B cell population includes either or both of reductions in IgE secretion and attenuation of the total number of IgE secreting B cells. Candidate doses are readily determined by the use of in vitro cell cultures or animal models.

Preparation of FCEH- and FCEL-Specific Polypeptides

The FCEH- or FCEL-specific polypeptides of this invention are made in conventional fashion, i.e., modifications of amino acid sequence are accomplished by commonly available DNA mutagenesis methods such as PCR amplification using primers bearing the mutants, or by M13 mutagenesis, followed by expression of the mutated DNA in recombinant host cells. The polypeptides also can be made by Merrifield or other in vitro methods of synthesis if they are sufficiently small (generally, under about 100 residues). However, the polypeptides preferably are made by recombinant methods. Selection of recombinant host cells, vectors, culture conditions and other parameters are not believed to be critical. In general, hosts, vectors and methods heretofore used in the recombinant expression of immunoglobulins (generally, IgGs) are also useful for the preparation of the polypeptide sequences of this invention. Preferably, mammalian cells such as myelomas, CHO, Cos, and the like are employed as hosts, and the vectors are constructed for secretory expression of the polypeptide. Recombinant expression systems facilitate the preparation of functional immunoglobulin variants containing FCEL- or FCEH-specific sequences since the host cells can be transformed with DNA encoding one heavy chain containing the FCEL- or FCEH-specific sequences and one light chain, each of which contains a variable domain for binding a first antigen, and an immunoglobulin that binds antigen and FCEL or FCEH recovered. Similarly, the same process is used with DNA encoding in addition another heavy chain containing the FCEL- or FCEH-specific domain and another light chain, each of which contain a variable domain for binding a second antigen, and a bivalent immunoglobulin recovered. Properly assembled immunoglobulin analogues are recovered by affinity chromatography on a matrix containing the two antigen(s).

The polypeptides of this invention are recovered from lysed recombinant cell culture or (when secreted) the culture supernatant. Substantial purification is achieved by passing cell free extracts which contain the polypeptides over an immobilized FCEL or FCEH receptor affinity matrix. Other methods heretofore used to purify IgE or other appropriate immunoglobulins are equally acceptable here, including immunoaffinity and (when appropriate) absorption on immobilized antigen.

Polypeptides of this invention which contain short sequences preferably are prepared using solid-phase synthesis, e.g. the method of Merrifield, J. Am. Chem. Soc. (1963) 85, 2149. However, other equivalent chemical syntheses known in the art are acceptable. The recombinant or in vitro synthesized polypeptides then are cross-linked to matrices (for use in diagnostic or preparatory procedures) or are placed into conformationally restrained structures. Known cyclizing procedures such as those described in PCT 90/01331 or Lys/Asp cyclization using Nα-Boc-amino acids on solid-phase support with Fmoc/9-fluorenylmethyl (Ofm) side-chain protection for Lys/Asp, followed by piperidine treatment and cyclization, are useful. Methods which depend upon cross-linking or cyclization through residue side chains may require that an extraneous residue be inserted at the C and/or N terminus of the AB-B or beta stand D domains, as the case may be, to provide a suitable cyclizing or cross-linking site.

Glu and Lys side chains also have been crosslinked in preparing cyclic or bicyclic peptides: the peptide is synthesized by solid phase chemistry on a p-methylbenzhydrylamine resin, the peptide is cleaved from the resin and deprotected. The cyclic peptide is formed using diphenylyphosphorylazide in diluted methylformamide. For an alternative procedure, see Schiller et al., *Peptide Protein Res.* (1985) 25, 171–177. See also U.S. Pat. No. 4,547,489.

Disulfide crosslinked or cyclized peptides are generated by conventional methods. The method of Pelton et al., (*J. Med Chem.* (1986) 29, 2370–2375) is suitable. Also useful are thiomethylene bridges (*Tetrahedron Letters* (1984) 25, 2067–2068). See also Cody et al., *J. Med Chem.* (1985) 28, 583. The C390 residue found in the C-terminal sequence of the AB-B domain is useful in cross-linking or cyclizing this domain.

Typically, extraneous residues which are to participate in cyclization or cross-linking are inserted at the N- and C-termini of the chosen AB-B or beta strand D sequence as part of the synthesis of the polypeptide precursor to be employed in the procedure. The desired cyclic or cross-linked peptides are purified by gel filtration followed by reversed-phase high pressure liquid chromatography or other conventional procedures. The peptides are sterilized by 0.2 $\mu$m filtration and formulated into conventional pharmacologically acceptable vehicles.

The compounds described in this invention may be the free acid or base or converted to salts of various inorganic and organic acids and bases. Such salts are within the scope of this invention. Examples of such salts include ammonium, metal salts like sodium, potassium, calcium and magnesium; salts with organic bases like dicyclohexylamine-N-methyl-D-glucamine and the like; and salts with amino acids such as arginine or lysine. Salts with inorganic and organic acids may be like prepared, for example, using hydrochloric, hydrobromic, sulfuric, phosphoric, trifluoroacetic, methanesulfonic, maleic, fumaric and the like. Non-toxic and physiologically compatible salts are particularly useful although other less desirable salts may have use in the processes of isolation and purification.

A number of methods are useful for the preparation of the salts described above and are known to those skilled in the art. For example, reaction of the free acid or free base form of a compound of Formula I with one or more molar equivalents of the desired acid or base in a solvent or solvent mixture in which the salt is insoluble; or in a solvent like water after which the solvent is removed by evaporation, distillation or freeze drying. Alternatively, the free acid or base form of the product may be passed over an ion exchange resin to form the desired salt, or one salt form of the product may be converted to another using the same general process.

Additional pharmaceutical methods may be employed to control the duration of action of the polypeptides of this invention. Controlled release preparations are achieved through the use of polymers which complex with or absorb the subject polypeptides. Controlled delivery is achieved by formulating the polypeptides into appropriate macromolecular articles (for example, those prepared from polyesters, polyamino acids, polyvinyl, polypyrrolidone, ethylenevinylacetate, methlycellulose, carboxymethylcellulose, or polyamine sulfate).

Alternatively, instead of entrapping the polypeptides in polymeric matrices, it is possible to entrap these materials in microcapsules prepared, for example, by coacervation techniques or by interfacial polymerization. Hydroxymethylcellulose or gelatin microcapsules and poly-(methylmethacrylate) microcapsules, respectively, are useful, as are in colloidal drug delivery systems (for example, liposomes, albumin microspheres, microemulsions, nano-particles and nanocapsules). See *Remington's Pharmaceutical Sciences* (1980).

EXAMPLE 1

Preparation of monoclonal antibodies to IgE

Eight monoclonal antibodies with the ability to block the binding of IgE to the FCEH were used. These monoclonal antibodies, referred to as MAE10–MAE17, were made in the following manner. Purified human IgE was prepared from supernatants of U266B1 cells (ATCC TIB 196) using affinity chromatography on a previously isolated anti-IgE antibody (Genentech MAE1). For MAE12, five BALB/c female mice, age six weeks, were immunized in their foot pads with 10 μg of the purified IgE in Ribi's adjuvant. Subsequent injections were done in the same manner one and three weeks after the initial immunizations. Three days after the final injection, the inguinal and popliteal lymph nodes were removed and pooled, and a single cell suspension was made by passing the tissue through steel gauze. For MAE14, MAE15, and MAE13 the immunizations were done in a similar manner except that for MAE13 30 μg of IgE per injection were used and IgE 315-S47 was used as a perfusion boost; for MAE14 and MAE15 five injections of 50 μg each were used; and the IgE immunogen for MAE17 was IgE 315-S47. For MAE10 and MAE11, injections were given subcutaneously in two doses of 100 μg and a final booster of 50 μg, and spleen cells were used for the fusions. The cells were fused at a 4:1 ratio with mouse myeloma P3X63-Ag8.653 (ATCC CRL 1580) in high glucose (DMEM) containing 50% w/v polyethylene glycol 4000.

Fused cells were plated at a density of $2 \times 10^5$ per well in 96 well tissue culture plates. After 24 hours HAT selective medium (hypoxanthine/aminopterin/thymidine, Sigma Chemical Company, # H0262) was added. Of 1440 wells plated, 365 contained growing cells after HAT selection.

Fifteen days after the fusion, supernatants were tested for the presence of antibodies specific for human IgE using an enzyme-linked immunosorbent assay (ELISA). The ELISA was performed as follows, with all incubations done at room temperature. Test plates (Nunc Immunoplate) were coated for 2 hours with rat anti-mouse IgG (Boehringer Mannheim, # 605-500) at 1 μg/ml in 50 Mm sodium carbonate buffer, Ph 9.6, then blocked with 0.5% bovine serum albumin in phosphate buffered saline (PBS) for 30 minutes, then washed four times with PBS containing 0.05% Tween 20 (PBST). Test supernatants were added and incubated two hours with shaking, then washed four times with PBST. Human IgE (purified from U266 cells as described above) was added at 0.5 μg/ml and incubated for one hour with shaking, then washed four times in PBST. Horseradish peroxidase conjugated goat anti-human IgE (Kirkegaard & Perry Labs, # 14-10-04, 0.5 mg/ml) was added at a 1:2500 dilution and incubated for one hour, then washed four times with PBST. The plates were developed by adding 100 μl/well of a solution containing 10 mg. of o-phenylenediamine dihydrochloride (Sigma Chemical Company # P8287) and 10 μl of a 30% hydrogen peroxide solution in 25 ml of phosphate citrate buffer Ph 5.0, and incubating for 15 minutes. The reaction was stopped by adding 100 μl/well of 2.5 M sulfuric acid. Data was obtained by reading the plates in an automated ELISA plate reader at an absorbance of 490 nm. For MAE12, 365 supernatants were tested and 100 were specific for human IgE. Similar frequencies of IgE specificity were obtained when screening for the other antibodies. All of the monoclonal antibodies described herein were of the IgG1 isotype except for MAE17, which was IgG2a.

Each of the IgE specific antibodies was further tested in cell-based and plate assays to select for antibodies which bound to IgE in such a way as to inhibit IgE binding to FCEH and which are not capable of binding to FCEH-bound IgE.

EXAMPLE 2

Preparation of Mutant IgE

Based on the model of IgE Fc by Padlan & Davies (*Mol. Immunol.* 23:1063 (1986), which is based on the crystal structure of human IgG1 Fc (Deisenhofer, *Biochem.* 20:2361–2370 [1981]), a series of mutants were designed which could be used to test the binding of human IgE to its receptors. These mutants are designated Emut 1–13, and are listed in Table 3 below. The Fcε3 domain is comprised of seven β-strands which form a β-sheet structure representative of all immunoglobulin domains; there are six loops which connect these seven β-strands. We refer to these loops by the 2 β-strands they connect, e.g. loop AB connects β-stands A and B. We have constructed mutants of human IgE in which we have substituted five of the Fcε3 domain loops with their counterparts from human IgG1 (Table 3, 1–5). The sixth loop contains the glycosylation site in both IgE and IgG and hence was not altered. One mutant, (Table 3, 6), was made by exchanging human Fcε3 β-strand D with its human IgG1 Fcgamma2 counterpart. Seven additional mutants, (Table 3, 7–13), consisted of the substitution of Ala residues into Fcε3 β-strands and a loop in Fcε2.

A human IgE gene was cloned from U266, a publicly available cell line. The gene was cloned into a previously described phagemid vector containing the human cytomegalovirus enhance and promoter, a 5' intron and sv40 polyadenylation signal (Gorman et al., *DNA and Prot. Eng. Techn.*, 2:3–10 [1990]). Mutagenesis was performed by the Kunkel method (T. A. Kunkel, *Proc. Natl. Acad. Sci. U.S.A.* 82:488–492 (1985) using buffers and enzymes supplied with the BioRad Muta-gene phagemid in vitro mutagenesis kit, together with oligonucleotides encoding the human IgG1 sequences shown in Table 3 below. Sequences of the mutant IgE DNAs were checked only at the site of mutation using $^{35}$S dideoxy sequencing.

TABLE 3

| Mutant | Kabat Residue No. (Structure)[1] | Human IgeE Fcε3 Seq. | Human IgG1 Fcγ2 Seq. |
|---|---|---|---|
| 1 | 377–385 (1AB) | FDLFIRKS (SEQ ID NO:2) | KDTLMISRT (SEQ ID NO:3) |
| 2 | 396–401 (1BC) | APSKGT (SEQ ID NO:4) | SHEDPQ (SEQ ID NO:5) |
| 3 | 407–420 (1CD) | SRASGKPVNHS (SEQ ID NO:6) | YVDGVQVHNAK (SEQ ID NO:7) |
| 4 | 444–453 (1EF) | GTRDWIEGET (SEQ ID NO:8) | LHQDWLDGKE (SEQ ID NO:9) |
| 5 | 465–469 (1FG) | RALM (SEQ ID NO:10) | APIE (SEQ ID NO:11) |
| 6 | 423–428 (βD) | KEEKQR (SEQ ID NO:12) | PREQQY (SEQ ID-NO:13) |
| 7 | 383–385 (1AB) | RKS (SEQ ID NO:18) | [AAA][2] (SEQ ID NO:19) |
| 8 | 387, 389 (βB) | T(I)T (SEQ ID NO:20) | [A(I)A][2] (SEQ ID NO:21) |
| 9 | 403, 405 (βC) | N(L)T (SEQ ID NO:22) | [A(L)A][2] (SEQ ID NO:23) |
| 10 | 438–440 (βE) | T(S)T (SEQ ID NO:24) | [A(S)A][2] (SEQ ID NO:25) |
| 11 | 455, 457, 459 (βF) | Q(C)R(V)T (SEQ ID NO:14) | [A(C)A(V)A][2] (SEQ ID NO:15) |
| 12 | 471, 473 (βG) | S(T)T (SEQ ID NO:26) | [A(T)A][2] (SEQ ID NO:27) |
| 13 | 329–331, 334–336 | QKH(WL)SDR (SEQ ID NO:16) | [AAA(WL)AAA][2] (SEQ ID NO:17) |

[1]loop = 1; B-strand = β
[2]Sequences in brackets are from mutants in which analine residues rather than IgG sequences were used to replace the IgE target sequence. Residues in parentheses were not altered in these mutants.

The mutant IgEs were transiently expressed in human embryonic kidney 293 cells (Gorman et al., supra), purified on a mouse anti-human IgE antibody affinity column and samples run using SDS-PAGE to ascertain that the mutant proteins were of the proper molecular weight.

EXAMPLE 3

Soluble FCEH binding assay

This assay is a sequential inhibition ELISA measuring binding to the FCEH only. In this assay, a monoclonal antibody against the FCEH is coated onto ELISA plates at a concentration of 1 μg/ml in 50 mM sodium carbonate pH 9.6 for two hours at room temperature, and blocked for two hours with PBS containing 0.5% bovine serum albumin (PBSA), then washed three times with ELISA wash buffer (0.05% Tween 20 in PBS). Recombinantly produced soluble FCEH is added at a concentration of 50 units/ml and incubated for one hour, then washed five times in ELISA wash buffer. Mutant IgE samples are then added to the wells and incubated for one to two hours. The excess mutant IgE is removed by aspiration, and biotinylated IgE is then added at 50 ng/ml for 15 minutes followed by five washes with ELISA wash buffer. Streptavidin conjugated to horseradish peroxidase (Sigma Chemical Company #S5512) was added at a 1:5000 dilution for 15 minutes, then washed three times with ELISA wash buffer. Color was developed with a tetramethyl benzidine peroxidase substrate system (Kirkegaard &. Perry Labs # 50-76-00, Lot. no. NA 18) for seven minutes at 25° C. The reaction was stopped by the addition of 1 M HCl. The ability of the mutant IgE to bind the FCEH is assessed by the degree to which the biotinylated IgE is prevented from binding. This assay is designed to test for any FCEH binding by the mutant IgE and is not meant to determine the affinity of the mutant for the FCEH relative to native IgE.

FACS based binding assays for U266 IgE mutants

Tissue culture supernatants from 293s cells transfected with U266 IgE cDNA were harvested at either 48 or 96 hours post transfection. Tissue culture supernatants were concentrated 5-x with Amicon Centriprep 30® centrifugal concentrators (30,000 MW cutoff). Concentrated supernatants were passed through a mouse monoclonal anti-U266 IgE affinity column (Genentech MAE1 coupled to CnBr-Sepharose). U266 IgE was eluted from the column with 3.0 M potassium cyanate in 50 mM tris buffer Ph 7.8. Eluate fractions containing protein as determined by O.D.280 nm were pooled and placed in Amicon Centricon 30® concentrators. Eluate buffer was exchanged for PBS by passing multiple volumes of PBS through the concentrator. The final volume of affinity purified supernatant ranged from 0.5–1 ml. Structural integrity of recombinant IgE mutants was analyzed on 1–12% SDS PAGE gels and compared with U266 IgE standard obtained from the U266 cell line. Mutants were also analyzed for the ability to bind to a series of monoclonal and IgE antibodies to further ascertain proper folding and structural identity with native IgE. The concentration of immunoreactive IgE for each IgE mutant was determined by a human IgE capture ELISA as follows. Nunc Immunoplate Maxisorp® plates (Nunc # 4-39451) were coated overnight at 4° C. with a Genentech murine IgG1 anti-U266 IgE. (MAE1) at 1 μg/ml in coat buffer (50 mM sodium carbonate buffer pH 9.6). Coat antibody was removed by three washes with ELISA wash buffer (0.05% Tween 20 (U.S. Biochemical Corporation # 20605) in PBS). Non-specific sites were blocked with ELISA diluent buffer (50 mM tris buffered saline containing 0.5% BSA (Sigma Chemical Company # A-7888), 0.05% Tween 20 and 2 mM EDTA) for two hours at 25° C. on an orbital shaker. Diuent buffer was removed with 3 washes of ELISA wash buffer. Serial two-fold dilutions of IgE mutants in ELISA diluent buffer were added to the plate. U266 IgE standard (lot 13068-46) was added at 1000, 500, 250, 125, 62.5, 31.3, and 15.6 ng/ml in duplicate as standards. Samples and standard were incubated two hours at 25° C. followed by three washes with ELISA wash buffer. IgE was detected with HRP conjugated Sheep anti-human IgE (ICN # N060-050-1) at 1:8000 in ELISA diluent buffer for 90 min. at 25° C. followed by 3 washes with ELISA wash buffer. HRP conjugate was developed with a tetramethyl benzidine peroxidase substrate system (Kirkegaard & Perry Labs. # 50-76-00, Lot. no. NA 18) for 7 minutes at 25° C. The reaction was stopped by the addition of 1 M HCl. The reaction product was analyzed with a dual wavelength spectrophotometer at 450 nm minus absorption at 570 nm. The U266 IgE standards were used to generate a standard curve and IgE concentrations of the sample were extrapolated by non-parametric linear regression analysis.

FcERI alpha (+) CHO 3D10 (FCEH expressing) and FcERII (CD23) (+) IM9 (FCEL expressing) B cell lines were used for the binding assays. The stably transfected CHO (duk−) cell clone 3D10 (JBC 265, 22079–22081, 1990) was maintained in Iscove's modified Dulbecco's media supplemented with 10% heat inactivated fetal calf serum, 80 µg/ml gentamicin sulfate and $5 \times 10^{-7}$ M methotrexate. The IM9 human B cell myeloma ATCC CCL 159. (Ann. N.Y. Acad. Sci. 190:221–234, 1972) was maintained in GIF base medium with 10% heat inactivated fetal bovine serum, penicillin, streptomycin (100 units/ml) and L-glutamine (2 mM). As a positive control to determine the level of CD23 on the surface of IM9 cells in each experiment, an aliquot of cells was stained with Becton Dickinson murine monoclonal Leu 20 (anti–CD23) at 10 µg/ml for 30 minutes at 4° C. followed by two washes in FACS buffer. The cells were then incubated with FITC conjugated F(ab')2 affinity purified goat anti-murine IgG at 5 µg/ml. Adherent CHO3D10 cells were removed from tissue culture dishes by incubation with 10 mM EDTA in PBS for 2 minutes at 37° C. Cells were counted, then resuspended in FACS buffer (0.1% BSA, 10 mM Na azide in PBS pH 7.4) at a concentration of $5 \times 10^6$/M]. CHO3D10 and Im9 cells ($5 \times 10^5$/aliquot) were incubated in 100 µl of FACS buffer containing U266 IgE standard or IgE mutants at 2 µg/ml for 30 minutes at 4° C. in 96 well microtiter plates followed by two washes with FACS buffer. As a control, cells were incubated in buffer alone or buffer containing 2 µg/ml human IgG1 (Behring Diagnostics # 400112, lot no. 801024). Cells were then incubated in 100 µl FACS buffer containing FITC conjugated rabbit anti-human IgE at 20 µg/ml (Accurate Chem. Co. # AXL 475F, lot.no. 040A) for 30 minutes at 4° C. followed by 3 washes with FACS buffer. 400 µl of buffer containing propidium iodide at 2 µg/ml was added to the cell suspension to stain dead cells. Cells were analyzed on a Becton Dickinson FACSCAN flow cytometer. Forward light scatter and 90 degree side scatter gates were set to analyze a homogeneous population of cells and dead cells which stained with propidium iodide were excluded from analysis. FITC positive cells (IgE binding) were analyzed relative to cells stained with FITC rabbit anti-H IgE alone.

The foregoing assays were used to determine the ability of the example 2 IgE analogues to bind to FCEH and FCEL. The results are set forth in Table 4.

TABLE 4

BINDING OF IGE AND IGE ANALOGUES TO FCEH AND FCEL

| Sample/Mutant | Conc. (ug/ml) | FCEH alpha % CHO 3D10(+) | FCEL (CD23) % IM9 (+) |
| --- | --- | --- | --- |
| U266 IgE | 10 | 90.3 | 92.5 |
| U266 IgE | 5 | 89.9 | 82.6 |
| U266 IgE | 0.5 | 59.6 | 4.6 |
| U266 IgE | 0.1 | 15.8 | 1.7 |
| 1 | 1.65[1] | 1.7 | 4.3 |
| 2 | 1.65 | 34.3 | 48.9 |
| 3 | 1.65 | 32.3 | 1.2 |
| 4 | 1.65 | 4.9 | 9.2 |
| 5 | 1.65 | 60.5 | 73.9 |
| 6 | 1.65 | 1.4 | 71.6 |
| 7 | 1.65 | 76.4 | 73.9 |
| 8 | 1.65 | 70.3 | 16.3 |
| 9 | 1.65 | 84.2 | 94.3 |
| 10 | 1.65 | 67.5 | 84.8 |
| 11 | 1.65 | 70.8 | 61.5 |
| 12 | 1.65 | 84.7 | 90.3 |
| 13 | 1.65 | 85.7 | 96.1 |
| dh 184 (+) | 1.65 | 83.8 | 21.1 |
| PA13[2] (control) | 10 | 1.3 | |

[1]Values based on quantitative ELISA. U266 was used as the standard and murine anti-$F_{C\epsilon}$ monoclonal antibody to capture.
[2]A CDR grafted human IgG.

Three mutant IgEs exhibited complete loss of binding to the FCEH receptor: mutants 1, 4 and 6. Mutant 6 altered β-strand D at the end of Fcε3 close to the Fcε2 domain. Mutants 1 and 4 involved alteration of two Fcε3 loops which are adjacent and near the Fcε4 domain. Note that mutant 7 is subset of mutant 1 in which the three C-terminal residues of loop AB have been changed to alanines (Table 3, 1 vs. 7). However, mutant 7 does not affect binding to FCEH. We interpret this to mean that either 1) FcεRI binds at least one of IgE residues 377–381 or 2) the extra residue in IgG1 loop AB (9 residues) substituted for IgE loop AB (8 residues) effected deformation of some adjacent binding determinant, possibly loop EF. That mutants 8 and 10 had no affect on FcεRI binding most likely means that the FCEH receptor does not protrude into the cavity bounded by loop AB and β-strand D.

Although mutant 4 had a Leu replacing Gly444 (Table 3), this should not affect the conformation of loop EF. Residue 444 is prior to the N-terminus of this α-helix. In addition, murine IgE has a Val at position 444 and rat IgE has an Asp. The two buried hydrophobic residues in the middle of the α-helix, W448 and I449, are retained in the substituted IgG1 loop (W448, L449) as is G451 which terminated the α-helix. Hence the conformation of loop EF should be similar in IgE and IgG1.

Mutants 2 and 3 exhibited decreased binding to FCEH. Since loop BC lies near β-strand D and loop CD is in the vicinity of loop EF, it is conceivable that one or two residues in loops BC and CD contact FCEH.

Five mutant IgEs exhibited loss of binding to the FCEL receptor: mutants 1, 3 4, 7 and 8. Mutants 1 and 4 were discussed above. Mutant 3 involved alteration of loop CD; in contrast to FCEH, loop CD evidently plays a major role in FCEL binding. Mutant 7, a subset of mutant 1 as discussed above, comprises the C-terminal portion of loop AB and is proximal to loop EF. Additionally, mutant 8 consists of replacement of two Thr residues (387,389) with Ala; these two residues are part of β-strand B which is at the bottom of the aforementioned cavity bounded by loop AB and β-strand D. Mutant 10 comprised a different two residues in this cavity (438,440) on β-strand E, which is adjacent to β-strand B. Since mutant 10 did not affect FCEL binding, we conclude that the FCEL receptor should have only a minimal incursion into cavity while the high affinity receptor does not intrude into the cavity.

In addition to a glycosylation site at Asn430 which corresponds to the glycosylation site in IgG Fc, human IgE contains another glycosylation site at Asn403. Mutant 9 converted Asn403 and Thr405 to alanines (Table 3). Loss of carbohydrate did not affect binding to either receptor.

Based on the information from mutants 1–13, we propose that FCEH and FCEL have binding sites on IgE Fc which are distinct but overlap. The low affinity receptor seems to interact with a relatively smaller portion of the IgE Fcε3 domain involving three adjacent loops: AB, CD and EF. In contrast, the high affinity receptor interacts with a larger portion of IgE Fcε3, which spans loop EF, β-strand D and, possibly, the N-terminal portion of loop AB. Portions of loops BC and CD in the vicinity of loop EF and β-strand D may also interact with FCEH. In addition, FCEL may protrude into the cavity bounded by loop AB and β-strand D (FIG. 4), whereas FCEH does not do so. Since we have not evaluated any mutants in FCε4 and only one in Fcε2 (mutant 13), it is possible that portions of these two domains play a role in IgE-receptor binding.

We claim:

1. A differential binding FcεRI antagonist IgE polypeptide comprising from 30 to 250 residues from native heavy chain Fc IgE, comprising:

a. an intact β-strand D-domain of native IgE; and b. a non-functional loop AB and/or β-strand B domain of native IgE;

and wherein:

(1) said polypeptide retains sufficient conformational integrity of native IgE to bind FcεRI with at least about 75% of the affinity with which native IgE binds FcεRI, but will not bind FcεRII with more than about 20% of the affinity which native IgE binds; and (2) said conformational integrity is conferred to the polypeptide by:

(A) the presence of a human IgE Fc4 or IgG Fc3 sequence; or (B) cyclizing.

2. The polypeptide of claim 1, which has an FceRI binding affinity which is at least 80% the binding affinity of native IgE.

3. The polypeptide of claim 2, which has a binding affinity for FceRII which is at most 10% that of native IgE.

4. The polypeptide of claim 1, which contains a modified IgE AB-B domain which contains at least one substitution, deletion, or inserted amino acid residue which renders the modified AB-B domain incapable of binding FceRII.

5. The polypeptide of claim 4, which contains an IgE beta strand D sequence or fragment thereof.

6. The polypeptide of claim 5, wherein at least one of IgE residues 382, 383, 384, 385, 387, 388, 389 or 390 is mutated.

7. The polypeptide of claim 6, wherein at least one of residues 383, 384, 385, 387 or 389 is mutated.

8. The polypeptide of claim 6, wherein the amino acid residue at position 383 is changed to Ala, Glu, Asp or Ser.

9. The polypeptide of claim 6, wherein the amino acid residue at position 384 is changed to an amino acid selected from the group consisting of Ala, Gly, Pro, Glu, Gln and Asp.

10. The polypeptide of claim 6, wherein the amino acid at position 385 is changed to an amino acid selected from the group consisting of Ala, Val, Ile, Leu, Phe and Thr.

11. The polypeptide of claim 5, wherein the amino acid at position 386 is changed to an amino acid selected from the group consisting of Gly, Ala, Ser, Thr, Asp, Glu, Asn, Gln, His, Lys, Arg and Trp.

12. The polypeptide of claim 6, wherein the amino acid residue at position 387 and/or 389 is independently changed to an amino acid selected from the group consisting of Gly, Ala, Val, Leu, Ile, Asp, Glu, Asn, Gln, His, Lys, Arg, Phe, Tyr and Trp.

13. The polypeptide of claim 12, wherein the amino acid residue at position 387 and/or 389 is changed to Ala.

14. The polypeptide of claim 5, which contains IgE residues 421 to 440.

15. The polypeptide of claim 1, which comprises a residue at its N- and/or C-terminus which provides for the formation of a covalent or non-covalent bond between the N- and C-terminus of the polypeptide.

16. The polypeptide of claim 15, wherein the residue which provides for the formation of a covalent bond is a cysteine residue.

17. The polypeptide of claim 5, wherein the beta strand D sequence contains at least one mutation which enhances FceRI binding.

18. The polypeptide of claim 1, which is an immunoglobulin.

19. The polypeptide of claim 18, which contains a variable domain which binds a predetermined antigen.

20. The polypeptide of claim 1, which contains at least 50 residues.

21. The polypeptide of claim 19, wherein the antigen is selected from the group consisting of: CD8, CD3 and a lymphoid cell surface antigen.

22. The polypeptide of claim 18, which contains an IgG sequence extending from the IgG CH1 hinge to Fc gamma 3.

23. The polypeptide of claim 1, which comprises IgE residues spanning 420 to 442 inclusive.

24. The polypeptide of claim 1, which comprises a cytotoxic polypeptide or enzyme.

25. The polypeptide of claim 18, which is an IgE analogue wherein the region spanning IgE residues 373 to 390 inclusive contains a deletion, substitution or addition mutation.

26. The polypeptide of claim 25, wherein the mutation is in the region spanning IgE residues 382 to 390, inclusive.

* * * * *

SEQUENCE LISTING (1) GENERAL INFORMATION:

(iii) NUMBER OF SEQUENCES: 27

(2) INFORMATION FOR SEQ ID NO:1:

(i) SEQUENCE CHARACTERISTICS:
      (A) LENGTH: 119 amino acids
      (B) TYPE: Amino Acid
      (D) TOPOLOGY: Linear (xi) SEQUENCE DESCRIPTION: SEQ ID NO:1:

```
Xaa Asp Ser Asn Pro Arg Gly Val Ser Ala Tyr Leu Ser Arg Pro
 1               5                  10                  15

Ser Pro Phe Asp Xaa Leu Phe Ile Arg Lys Ser Pro Thr Ile Thr
                20                  25                  30

Cys Leu Val Val Asp Leu Ala Pro Ser Lys Gly Thr Val Asn Leu
                35                  40                  45

Thr Trp Ser Arg Xaa Ala Ser Xaa Xaa Gly Lys Pro Val Asn His
                50                  55                  60

Ser Thr Arg Lys Glu Glu Lys Gln Arg Xaa Asn Xaa Xaa Gly Thr
                65                  70                  75

Leu Thr Val Thr Ser Thr Leu Pro Val Gly Thr Arg Asp Trp Ile
                80                  85                  90

Glu Gly Glu Thr Tyr Gln Cys Arg Val Thr His Pro His Leu Pro
                95                 100                 105

Arg Ala Leu Xaa Met Arg Ser Thr Thr Lys Thr Ser Gly Pro
               110                 115             119
```

(2) INFORMATION FOR SEQ ID NO:2:

(i) SEQUENCE CHARACTERISTICS:
      (A) LENGTH: 8 amino acids
      (B) TYPE: Amino Acid
      (D) TOPOLOGY: Linear (xi) SEQUENCE DESCRIPTION: SEQ ID NO:2:

```
Phe Asp Leu Phe Ile Arg Lys Ser
 1               5           8
```

(2) INFORMATION FOR SEQ ID NO:3:

(i) SEQUENCE CHARACTERISTICS:
      (A) LENGTH: 9 amino acids
      (B) TYPE: Amino Acid
      (D) TOPOLOGY: Linear (xi) SEQUENCE DESCRIPTION: SEQ ID NO:3:

Lys Asp Thr Leu Met Ile Ser Arg Thr
 1               5               9

(2) INFORMATION FOR SEQ ID NO:4:

(i) SEQUENCE CHARACTERISTICS:
        (A) LENGTH: 6 amino acids
        (B) TYPE: Amino Acid
        (D) TOPOLOGY: Linear (xi) SEQUENCE DESCRIPTION: SEQ ID NO:4:

Ala Pro Ser Lys Gly Thr
 1               5   6

(2) INFORMATION FOR SEQ ID NO:5:

(i) SEQUENCE CHARACTERISTICS:
        (A) LENGTH: 6 amino acids
        (B) TYPE: Amino Acid
        (D) TOPOLOGY: Linear (xi) SEQUENCE DESCRIPTION: SEQ ID NO:5:

Ser His Glu Asp Pro Gln
 1               5   6

(2) INFORMATION FOR SEQ ID NO:6:

(i) SEQUENCE CHARACTERISTICS:
        (A) LENGTH: 11 amino acids
        (B) TYPE: Amino Acid
        (D) TOPOLOGY: Linear (xi) SEQUENCE DESCRIPTION: SEQ ID NO:6:

Ser Arg Ala Ser Gly Lys Pro Val Asn His Ser
 1               5                   10  11

(2) INFORMATION FOR SEQ ID NO:7:

(i) SEQUENCE CHARACTERISTICS:
        (A) LENGTH: 11 amino acids
        (B) TYPE: Amino Acid
        (D) TOPOLOGY: Linear (xi) SEQUENCE DESCRIPTION: SEQ ID NO:7:

Tyr Val Asp Gly Val Gln Val His Asn Ala Lys
 1               5                   10  11

(2) INFORMATION FOR SEQ ID NO:8:

(i) SEQUENCE CHARACTERISTICS:
        (A) LENGTH: 10 amino acids
        (B) TYPE: Amino Acid
        (D) TOPOLOGY: Linear (xi) SEQUENCE DESCRIPTION: SEQ ID NO:8:

Gly Thr Arg Asp Trp Ile Glu Gly Glu Thr
 1               5                   10

(2) INFORMATION FOR SEQ ID NO:9:

(i) SEQUENCE CHARACTERISTICS:
        (A) LENGTH: 10 amino acids
        (B) TYPE: Amino Acid
        (D) TOPOLOGY: Linear (xi) SEQUENCE DESCRIPTION: SEQ ID NO:9:

```
Leu His Gln Asp Trp Leu Asp Gly Lys Glu
  1               5                  10
```

(2) INFORMATION FOR SEQ ID NO:10:

(i) SEQUENCE CHARACTERISTICS:
        (A) LENGTH: 4 amino acids
        (B) TYPE: Amino Acid
        (D) TOPOLOGY: Linear (xi) SEQUENCE DESCRIPTION: SEQ ID NO:10:

```
Arg Ala Leu Met
  1           4
```

(2) INFORMATION FOR SEQ ID NO:11:

(i) SEQUENCE CHARACTERISTICS:
        (A) LENGTH: 4 amino acids
        (B) TYPE: Amino Acid
        (D) TOPOLOGY: Linear (xi) SEQUENCE DESCRIPTION: SEQ ID NO:11:

```
Ala Pro Ile Glu
  1           4
```

(2) INFORMATION FOR SEQ ID NO:12:

(i) SEQUENCE CHARACTERISTICS:
        (A) LENGTH: 6 amino acids
        (B) TYPE: Amino Acid
        (D) TOPOLOGY: Linear (xi) SEQUENCE DESCRIPTION: SEQ ID NO:12:

```
Lys Glu Glu Lys Gln Arg
  1           5   6
```

(2) INFORMATION FOR SEQ ID NO:13:

(i) SEQUENCE CHARACTERISTICS:
        (A) LENGTH: 6 amino acids
        (B) TYPE: Amino Acid
        (D) TOPOLOGY: Linear (xi) SEQUENCE DESCRIPTION: SEQ ID NO:13:

```
Pro Arg Glu Gln Gln Tyr
  1           5   6
```

(2) INFORMATION FOR SEQ ID NO:14:

(i) SEQUENCE CHARACTERISTICS:
        (A) LENGTH: 5 amino acids
        (B) TYPE: Amino Acid
        (D) TOPOLOGY: Linear (xi) SEQUENCE DESCRIPTION: SEQ ID NO:14:

```
Gln Cys Arg Val Thr
  1           5
```

(2) INFORMATION FOR SEQ ID NO:15:

(i) SEQUENCE CHARACTERISTICS:
        (A) LENGTH: 5 amino acids
        (B) TYPE: Amino Acid
        (D) TOPOLOGY: Linear (xi) SEQUENCE DESCRIPTION: SEQ ID NO:15:

```
Ala Cys Ala Val Ala
  1           5
```

(2) INFORMATION FOR SEQ ID NO:16:

(i) SEQUENCE CHARACTERISTICS:
        (A) LENGTH: 8 amino acids
        (B) TYPE: Amino Acid
        (D) TOPOLOGY: Linear (xi) SEQUENCE DESCRIPTION: SEQ ID NO:16:

Gln Lys His Trp Leu Ser Asp Arg
 1             5         8

(2) INFORMATION FOR SEQ ID NO:17:

(i) SEQUENCE CHARACTERISTICS:
        (A) LENGTH: 8 amino acids
        (B) TYPE: Amino Acid
        (D) TOPOLOGY: Linear (xi) SEQUENCE DESCRIPTION: SEQ ID NO:17:

Ala Ala Ala Trp Leu Ala Ala Ala
 1             5         8

(2) INFORMATION FOR SEQ ID NO:18:

(i) SEQUENCE CHARACTERISTICS:
        (A) LENGTH: 3 amino acids
        (B) TYPE: Amino Acid
        (D) TOPOLOGY: Linear (xi) SEQUENCE DESCRIPTION: SEQ ID NO:18:

Arg Lys Ser
 1     3

(2) INFORMATION FOR SEQ ID NO:19:

(i) SEQUENCE CHARACTERISTICS:
        (A) LENGTH: 3 amino acids
        (B) TYPE: Amino Acid
        (D) TOPOLOGY: Linear (xi) SEQUENCE DESCRIPTION: SEQ ID NO:19:

Ala Ala Ala
 1     3

(2) INFORMATION FOR SEQ ID NO:20:

(i) SEQUENCE CHARACTERISTICS:
        (A) LENGTH: 3 amino acids
        (B) TYPE: Amino Acid
        (D) TOPOLOGY: Linear (xi) SEQUENCE DESCRIPTION: SEQ ID NO:20:

Thr Ile Thr
 1     3

(2) INFORMATION FOR SEQ ID NO:21:

(i) SEQUENCE CHARACTERISTICS:
        (A) LENGTH: 3 amino acids
        (B) TYPE: Amino Acid
        (D) TOPOLOGY: Linear (xi) SEQUENCE DESCRIPTION: SEQ ID NO:21:

Ala Ile Ala
 1     3

(2) INFORMATION FOR SEQ ID NO:22:

(i) SEQUENCE CHARACTERISTICS:
        (A) LENGTH: 3 amino acids
        (B) TYPE: Amino Acid
        (D) TOPOLOGY: Linear (xi) SEQUENCE DESCRIPTION: SEQ ID NO:22:

Asn Leu Thr
 1       3

(2) INFORMATION FOR SEQ ID NO:23:

(i) SEQUENCE CHARACTERISTICS:
        (A) LENGTH: 3 amino acids
        (B) TYPE: Amino Acid
        (D) TOPOLOGY: Linear (xi) SEQUENCE DESCRIPTION: SEQ ID NO:23:

Ala Leu Ala
 1       3

(2) INFORMATION FOR SEQ ID NO:24:

(i) SEQUENCE CHARACTERISTICS:
        (A) LENGTH: 3 amino acids
        (B) TYPE: Amino Acid
        (D) TOPOLOGY: Linear (xi) SEQUENCE DESCRIPTION: SEQ ID NO:24:

Thr Ser Thr
 1       3

(2) INFORMATION FOR SEQ ID NO:25:

(i) SEQUENCE CHARACTERISTICS:
        (A) LENGTH: 3 amino acids
        (B) TYPE: Amino Acid
        (D) TOPOLOGY: Linear (xi) SEQUENCE DESCRIPTION: SEQ ID NO:25:

Ala Ser Ala
 1       3

(2) INFORMATION FOR SEQ ID NO:26:

(i) SEQUENCE CHARACTERISTICS:
        (A) LENGTH: 3 amino acids
        (B) TYPE: Amino Acid
        (D) TOPOLOGY: Linear (xi) SEQUENCE DESCRIPTION: SEQ ID NO:26:

Ser Thr Thr
 1       3

(2) INFORMATION FOR SEQ ID NO:27:

(i) SEQUENCE CHARACTERISTICS:
        (A) LENGTH: 3 amino acids
        (B) TYPE: Amino Acid
        (D) TOPOLOGY: Linear (xi) SEQUENCE DESCRIPTION: SEQ ID NO:27:

Ala Thr Ala
 1       3